(12) United States Patent
Halasa et al.

(10) Patent No.: US 7,714,089 B2
(45) Date of Patent: May 11, 2010

(54) FUNCTIONALIZED MONOMERS AND FUNCTIONALIZED RUBBERY POLYMERS MADE THEREWITH

(75) Inventors: Adel Farhan Halasa, Bath, OH (US); Wen-Liang Hsu, Cuyahoga Falls, OH (US); Leh-Yeh Hsu, legal representative, Cuyahoga Falls, OH (US); Shingo Futamura, Wadsworth, OH (US); Joe Zhou, Bartlesville, OK (US); Chad Aaron Jasiunas, Copley, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 214 days.

(21) Appl. No.: 11/955,453

(22) Filed: Dec. 13, 2007

(65) Prior Publication Data

US 2009/0156769 A1    Jun. 18, 2009

(51) Int. Cl.
| | |
|---|---|
| C08F 236/14 | (2006.01) |
| C08F 226/06 | (2006.01) |
| C08F 230/02 | (2006.01) |
| C07C 323/25 | (2006.01) |
| C07F 7/10 | (2006.01) |
| C08F 2/22 | (2006.01) |

(52) U.S. Cl. .................. 526/288; 526/260; 526/263; 526/274; 526/279; 526/336; 526/338; 546/184; 546/248; 544/178; 564/15; 564/440; 556/407; 556/413; 548/574; 548/579

(58) Field of Classification Search ................ 526/260, 526/263, 274, 279, 288, 338, 336; 556/407, 556/413; 564/440, 15; 544/178; 546/184, 546/248; 548/574, 579
See application file for complete search history.

(56) References Cited

U.S. PATENT DOCUMENTS

| | | | |
|---|---|---|---|
| 3,472,845 A | 10/1969 | Thiele | |
| 4,732,946 A | 3/1988 | Killat et al. | |
| 4,857,599 A | 8/1989 | Tomalia et al. | |
| 4,935,471 A | 6/1990 | Halasa et al. | |
| 6,310,164 B1 | 10/2001 | Morizono et al. | |
| 6,777,026 B2 | 8/2004 | Halladay et al. | |
| 6,844,412 B2 | 1/2005 | Halladay | |
| 6,889,735 B2 | 5/2005 | Frank et al. | |
| 6,901,982 B2 * | 6/2005 | Halasa et al. | ............... 152/450 |
| 6,933,358 B2 | 8/2005 | Halasa et al. | |
| 7,183,354 B2 | 2/2007 | Halladay et al. | |
| 2002/0068796 A1 | 6/2002 | Frank et al. | |
| 2003/0152790 A1 | 8/2003 | Halladay | |
| 2004/0018312 A1 | 1/2004 | Halladay | |
| 2004/0020576 A1 | 2/2004 | Frank et al. | |
| 2004/0063933 A1 | 4/2004 | Rodewald et al. | |
| 2004/0068036 A1 | 4/2004 | Halladay et al. | |

FOREIGN PATENT DOCUMENTS

JP    08-012681    1/1996

OTHER PUBLICATIONS

Marie E. Kraft and Carmelinda A. Juliano, Studies on the Use of Bidentate Ligands in the Directed Pauson-Khand Reaction, J. Org. Chem. 1992, vol. 57, pp. 5106-5115.
European Patent Office, European Search Report in corresponding EP Patent Application Serial No. 08170779.6-2103, issued Apr. 17, 2009, 6 pages.

* cited by examiner

*Primary Examiner*—Fred M Teskin
(74) *Attorney, Agent, or Firm*—Wood, Herron & Evans, L.L.P.

(57) ABSTRACT

Rubbery polymers can be formed having the general formula:

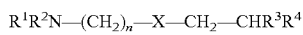

$$R^1R^2N-(CH_2)_n-X-CH_2-CHR^3R^4$$

wherein $R^1$ and $R^2$ are independently selected from a group consisting of alkyls, cycloalkyls, alkenyls, cycloalkenyls, aryls, phenyls, heterocycles, acyls, and silanes, or $R^1$ in combination with $R^2$ forms a heterocyclic ring; n is an integer from 1 to 20; X is selected from a group consisting of sulfur, a phosphorus moiety, and a silicon moiety; $R^3$ and $R^4$ are one of hydrogen, alkyls, alkenyls, and at least one of which includes reactive unsaturation such as an alkenyl group. Moreover, this invention discloses a process of making functionalized rubbery polymers from the functionalized monomers.

22 Claims, No Drawings

FUNCTIONALIZED MONOMERS AND FUNCTIONALIZED RUBBERY POLYMERS MADE THEREWITH

FIELD OF THE INVENTION

The present invention is directed to preparing functionalized monomers that are incorporated into polymers to form corresponding functionalized rubbery polymers, such as for use in tire treads.

BACKGROUND OF THE INVENTION

Tires require good wet skid resistance, low rolling resistance, tear strength, and good wear characteristics. It has traditionally been difficult to improve the wear characteristics of a tire without sacrificing wet skid resistance and traction characteristics. These properties depend, to a great extent, on the dynamic viscoelastic properties of the rubbery polymers utilized in making the tire.

In order to reduce the rolling resistance and to improve the treadwear characteristics of tires, rubbery polymers having a high rebound have traditionally been utilized in making tire tread rubber compounds. On the other hand, in order to increase the wet skid resistance of a tire, rubbery polymers that undergo a large energy loss have generally been utilized in the tread of the tire. In order to balance these two viscoelastically inconsistent properties, mixtures of various types of synthetic and natural rubber are normally utilized in tire treads. For instance, various mixtures of styrene-butadiene rubber (SBR) and polybutadiene rubber are commonly used as a rubbery material for automobile tire treads.

It is desirable for synthetic rubbers to exhibit low levels of hysteresis. This is particularly important in the case of rubbery polymers that are used in tire tread compounds. Such polymers are normally compounded with sulfur, carbon black, accelerators, antidegradants and other desired rubber chemicals and are then subsequently vulcanized or cured into the form of a useful article. The physical properties of such cured rubbery polymers depend in part upon the degree to which the fillers, such as carbon black or silica, are homogeneously dispersed throughout the polydiene rubber. This is in turn related to the affinity of the carbon black or silica to the rubber.

This homogenous dispersion, which is affected by the level of affinity between the filler and the polymer, can be of practical importance in improving the physical characteristics of rubber articles that are made utilizing polydiene rubbers. For example, the rolling resistance and tread wear characteristics of tires can be improved by increasing the affinity of carbon black to the rubbery polymers utilized therein. Therefore, it would be highly desirable to improve the affinity of a given rubbery polymer for carbon black and/or silica. This is because a better dispersion of carbon black throughout polydiene rubbers, which are utilized in compounding tire tread compositions, results in a lower hysteresis value and consequently tires made therefrom have lower rolling resistance. Accordingly, improving the affinity of the rubbery polymer to the filler, such as carbon black and silica is extremely important in reducing hysteresis.

One manner to attain improved interaction of rubbery polymers with fillers is to functionalize them. Such rubbery polymers can be functionalized with various compounds, such as amines. U.S. Pat. No. 4,935,471 discloses a process for preparing a polydiene having a high level of affinity for carbon black which comprises a capping agent selected from a group consisting of (a) halogenated nitrites, (b) heterocyclic aromatic nitrogen containing compounds, and (c) alkyl benzoates. Moreover, U.S. Pat. No. 4,935,471 discloses that lithium amides are preferred initiators. This combination provides polymer chains with polar groups at both terminal ends of the polymer chains.

Another approach to improve the affinity of a given rubbery polymer for carbon black and/or silica would be to incorporate functional groups throughout the polymeric chain. This incorporation can be achieved by forming rubbery polymers from a mixture of monomers, of which at least one of the monomers is functionalized, for example, an amine.

Therefore, what is needed are new functionalized monomers and methods for preparing and polymerizing such functionalized monomers to produce functionalized rubbery polymers, without the requirements of masking and unmasking the functional group, or of adding the functionality only after polymerization, for example.

SUMMARY OF THE INVENTION

This invention provides functionalized monomers and methods for preparing and polymerizing such functional group-bearing monomers to prepare functionalized rubber polymers and co-polymers.

According to this invention, functionalized monomers are formed having the following formula: $R^1R^2N-(CH_2)_n-X-CH_2-CHR^3R^4$, wherein $R^1$ and $R^2$ are independently selected from a group consisting of alkyls, cycloalkyls, alkenyls, cycloalkenyls, aryls, phenyls, heterocycles, acyls, and silanes, or $R^1$ in combination with $R^2$ forms a heterocyclic ring; n is an integer from 1 to 20; X is selected from a group consisting of sulfur, a phosphorus moiety, and a silicon moiety; $R^3$ and $R^4$ are selected from a group consisting of hydrogen, alkyls, alkenyls, and aryls; and at least one of $R^3$ and $R^4$ have reactive unsaturation such as an alkenyl group.

Another aspect of the invention involves preparing the functionalized rubbery polymers, at least in part, from the functionalized monomers. The functionalized rubbery polymer can be a polymer of at least one conjugated diene monomer or vinyl aromatic monomer, and the above functionalized monomer.

Another aspect of the invention is the method comprising polymerizing at least one conjugated diene monomer or vinyl aromatic monomer with the above functionalized monomer.

The resulting functionalized rubbery polymers and functionalized copolymers may be used as is or blended with other materials to make a variety of new products, including adhesives, sealants, surfactants, elastomers, ionomers for, e.g., coatings and membranes, and may also be employed as functionalized polyolefin precursors. The resulting functionalized polymers or functionalized polymer blends may be quaternized, hydrogenated, cross-linked, or subject to other known polymer reactions to enhance properties for other specific applications, such as described in detail herein.

Additional objects and advantages of the invention will be set forth in part in the description which follows, and in part will be obvious from the description, or may be learned by the practice of the invention. The objects and advantages of the invention will be attained by means of the instrumentalities and combinations particularly pointed out in the appended claims.

DETAILED DESCRIPTION

According to one embodiment of the present invention, rubbery polymers are formed by polymerization of a functionalized monomer with one or more conjugated diene monomers. The functionalized monomer has the following formula:

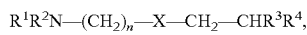

wherein $R^1$ and $R^2$ are independently selected from a group consisting of alkyls, cycloalkyls, alkenyls, cycloalkenyls, aryls, phenyls, heterocycles, acyls, and silanes, or $R^1$ in combination with $R^2$ forms a heterocyclic ring; n is an integer from 1 to 20; X is selected from a group consisting of sulfur, a phosphorus moiety, and a silicon moiety; $R^3$ and $R^4$ are selected from a group consisting of hydrogen, alkyls, alkenyls, and aryls; and at least one of $R^3$ and $R^4$ includes unsaturation reactive with other unsaturated monomers to polymerize. This will typically include an alkenyl group.

Exemplary embodiments include wherein $R^1$ and $R^2$ are the same or different and are selected from the group consisting of $C_1$-$C_{10}$ alkyl, oxygen substituted $C_1$-$C_{10}$ alkyl, and nitrogen substituted $C_1$-$C_{10}$ alkyl. In another embodiment, $R^1$ and $R^2$ represent a heterocyclic ring selected from the group of aziridine, azetidine, diazetidine, pyrrolidine, piperidine, piperazine, or morpholine moiety. In still another embodiment, $R^3$, $R^4$, or both are an aryl group at least one of which is substituted with an alkenyl moiety. In yet another embodiment, $R^3$ is either hydrogen or methyl; and $R^4$ is a aryl moiety substituted in the ortho, meta, or para position with an alkenyl moiety selected from the group consisting of ethylene and isopropylene, and optionally, $R^1$ and $R^2$ are selected from the group consisting of methyl, ethyl, propyl, butyl, pentyl, hexyl, phenyl, or benzyl.

The functionalized monomer can be prepared by employing a variant of the Michael reaction. Classically, the Michael reaction is the addition of an enolate of a ketone or aldehyde to an α,β-unsaturated carbonyl compound at the β carbon. Variants of the Michael reaction are known whereby nitrogen, oxygen, sulfur, phosphorus, and silicon nucleophiles will react in a similar regioselective manner.

Under appropriate conditions, these Michael reaction-type nucleophiles which are tethered to an amino group, will react with, for example, divinylbenzene or diisopropenylbenzene to form a functionalized styrene monomer. According to the present invention, sulfa-, silyl-, and phospha-Michael reactions are utilized to form amino-functionalized monomers.

More particularly, the amine functionalized unsaturated monomer is formed by reacting the following compound:

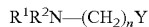

wherein Y represents Si, S, or P having at least one reactive hydrogen with an alkyl lithium compound catalyst, such as n-butyl lithium and a polyunsaturated compound such as di-vinyl benzene or di-isopropenyl benzene to form a functionalized unsaturated monomer. In particular, one mole of the amine is combined with one mole of the polyunsaturated compound dissolved in solvent, such as hexane and cooled to about 10° C. Approximately 30 mmoles of the butyl lithium is added per mole of the amine, and allowed to react for about an hour, at which time the solvent is evaporated, the residue is distilled under vacuum and the product isolated.

The functionalized monomers of this invention can be copolymerized into virtually any type of rubbery polymer. In most cases the functionalized monomer will be copolymerized with at least one conjugated diene monomer. Optionally, other monomers that are copolymerizable with conjugated diene monomers, such as vinyl aromatic monomers, can also be included in the polymerization. In any case, typically from about 0.05 percent by weight (based on the total weight of monomers) to about 20 weight percent of the functionalized monomer will be included in the polymerization. More typically, from about 0.1 percent by weight to about 10 percent by weight of the functionalized monomer will be included in the rubbery polymer. Good results can normally be attained by including 0.1 percent by weight to about 5 percent by weight of the functionalized monomer in the rubbery polymer.

Polymerization and recovery of polymer are suitably carried out according to various methods suitable for diene monomer polymerization processes. This includes batchwise, semi-continuous, or continuous operations under conditions that exclude air and other atmospheric impurities, particularly oxygen and moisture. The polymerization of the functionalized monomers of the invention may also be carried out in a number of different polymerization reactor systems, including but not limited to bulk polymerization, vapor phase polymerization, solution polymerization, suspension polymerization, emulsion polymerization, and precipitation polymerization systems. The commercially preferred methods of polymerization are solution polymerization and emulsion polymerization.

The polymerization reaction may use a free radical initiator, a redox initiator, an anionic initiator, a cationic initiator, or a Ziegler-Natta catalyst system. The initiation system generally depends upon the particular monomers being polymerized and the desired characteristics of the rubbery polymer being synthesized. In emulsion polymerizations, free radical initiators are typically utilized. In solution polymerizations, Ziegler-Natta catalyst systems or anionic initiators, such as alkyl lithium compounds, are typically employed to initiate the polymerization. An advantage of free radical polymerization is that reactions can typically be carried out under less rigorous conditions than ionic polymerizations. Free radical initiation systems also exhibit a greater tolerance of trace impurities.

Examples of free radical initiators that are useful are those known as "redox" initiators, such as combinations of chelated iron salts, sodium formaldehyde sulfoxylate, and organic hydroperoxides. Representative of organic hydroperoxides are cumene hydroperoxide, paramenthane hydroperoxide, and tertiary butyl hydroperoxide. In one example, tertiary butyl hydroperoxide (t-BHP), tertiary butyl peracetate (t-BPA) and "azo" initiators, such as azobisiobutyronitrile (AIBN), are used.

The reaction temperature is typically maintained in the range of 0° C. to 150° C. Temperatures between about 20° C. and 80° C. are generally preferred. The reaction pressure is not critical. It is typically only sufficiently high to maintain liquid phase reaction conditions; it may be autogenic pressure, which will vary depending upon the components of the reaction mixture and the temperature, or it may be higher, e.g., up to 1000 psi.

In batch operations, the polymerization time of functionalized diene monomers can be varied as desired; it may vary, for example, from a few minutes to several days. Polymerization in batch processes may be terminated when monomer is no longer absorbed, or earlier, if desired, e.g., if the reaction mixture becomes too viscous. In continuous operations, the polymerization mixture may be passed through a reactor of any suitable design. The polymerization reactions in such cases are suitably adjusted by varying the residence time. Residence times vary with the type of reactor system and range, for example, from 10 to 15 minutes to 24 or more hours.

The concentration of monomers in the reaction mixture may vary upward from 5 percent by weight of the reaction mixture, depending on the conditions employed. In another example, the range is from about 20 to about 80 percent by weight.

The polymerization reactions may be carried out in a suitable solvent that is liquid under the conditions of reaction and relatively inert. The solvent may have the same number of carbon atoms per molecule as the diene reactant or it may be in a different boiling range. In one example, the solvents include alkane and cycloalkane hydrocarbons. Other suitable solvents are, for example, hexane, cyclohexane, methylcyclohexane, or various saturated hydrocarbon mixtures. Aromatic hydrocarbons such as benzene, toluene, isopropylbenzene, xylene, or halogenated aromatic compounds such as chlorobenzene, bromobenzene, or orthodichlorobenzene may also be employed. Still other useful solvents include tetrahydrofuran and dioxane.

Conventional emulsion recipes may also be employed with the present invention; however, some restrictions and modifications may arise either from the polymerizable monomer itself, or the polymerization parameters. Ionic surfactants, known in the art, including sulfonate detergents and carboxylate, sulfate, and phosphate soaps are useful in this invention. The level of ionic surfactant is computed based upon the total weight of the organic components and may range from about 2 to 30 parts by weight of ionic surfactant per 100 parts by weight of organic components.

The polymerization generally is carried out to complete functionalized monomer conversion to incorporate essentially all of the polymerizable functional group-bearing monomer. Incremental addition, or a chain transfer agent, may be used in order to avoid excessive gel formation. Such minor modifications are within the skill of the artisan. After the polymerization is complete, the polymer is recovered from a slurry or solution of the polymer. A simple filtration may be adequate to separate polymer from diluent. Other means for separating polymer from diluent may be employed. The polymer may be treated, separately or while slurried in the reaction mixture, in order to separate residues. Such treatment may be with alcohols such as methanol, ethanol, or isopropanol, with acidified alcohols, or with other similar polar liquids. In many cases the polymers are obtained in hydrocarbon solutions and the polymer can be recovered by coagulation with acidified alcohol, e.g., rapidly stirred methanol or isopropanol containing 2% hydrochloric acid. Following this initial coagulation, the polymers may be washed several more times in methanol.

Examples of comonomers that are useful in the practice of this invention are diene monomers such as 1,3-butadiene, isoprene, and hexadienes. One may, in addition to the diene monomers, use a vinyl monomer such as divinylbenzene, diisopropenylbenzene, styrene, α-methylstyrene, divinyl benzene, vinyl chloride, vinyl acetate, vinylidene chloride, methyl methacrylate, ethyl acrylate, vinylpyridine, acrylonitrile, methacrylonitrile, methacrylic acid, itaconic acid and acrylic acid. Mixtures of different functionalized monomers and mixtures of different comonomers may be used. The functionalized monomer charge ratio by weight is normally from about 0.1/99.9 to 10.0/90.0 functionalized monomer to comonomer (including any additional vinyl monomer). A charge ratio by weight of about 0.1/99.9 to about 5/95 is preferred with 1/99 to 5/95 the most preferred. Ratios will vary depending on the amount of chemical functionality desired to be incorporated and on the reactivity ratios of the monomers in the particular polymerization system used.

The functionalized monomers of this invention offer a unique ability to randomly copolymerize with conjugated diene monomers in solution polymerizations that are conducted at temperatures of 20° C. or higher. The functionalized monomers of this invention can be incorporated into virtually any type of rubbery polymer that is capable of being made by solution polymerization with an anionic initiator or Zeigler-Natta type of catalyst. The polymerization employed in synthesizing the rubbery polymers will normally be carried out in a hydrocarbon solvent. Such hydrocarbon solvents are comprised of one or more aromatic, paraffinic or cycloparaffinic compounds. These solvents will normally contain from about 4 to about 10 carbon atoms per molecule and will be liquid under the conditions of the polymerization. Some representative examples of suitable organic solvents include pentane, isooctane, cyclohexane, methylcyclohexane, isohexane, n-heptane, n-octane, n-hexane, benzene, toluene, xylene, ethylbenzene, diethylbenzene, isobutylbenzene, petroleum ether, kerosene, petroleum spirits, petroleum naphtha, and the like, alone or in admixture.

In the solution polymerization, there will normally be from about 5 to about 30 weight percent monomers in the polymerization medium. Such polymerization media are, of course, comprised of the organic solvent and monomers. In another example, the polymerization medium may contain from about 10 to about 25 weight percent monomers. In another example, the polymerization medium may contain about 15 to about 20 weight percent monomers.

The rubbery polymers can be made by random copolymerization of the functionalized monomer with a conjugated diene monomer or by the random terpolymerization of the functionalized monomer with a conjugated diene monomer and a vinyl aromatic monomer. It is, of course, also possible to make such rubbery polymers by polymerizing a mixture of conjugated diene monomers with one or more ethylenically unsaturated monomers, such as vinyl aromatic monomers. The conjugated diene monomers which can be utilized in the synthesis of rubbery polymers which can be coupled in accordance with this invention generally contain from 4 to 12 carbon atoms. Those containing from 4 to 8 carbon atoms are generally preferred for commercial purposes. For similar reasons, 1,3-butadiene and isoprene are the most commonly utilized conjugated diene monomers. Some additional conjugated diene monomers that can be utilized include 2,3-dimethyl-1,3-butadiene, piperylene, 3-butyl-1,3-octadiene, 2-phenyl-1,3-butadiene, and the like, alone or in admixture.

Some representative examples of ethylenically unsaturated monomers that can potentially be polymerized in rubbery polymers that contain the functionalized monomers of this invention include alkyl acrylates, such as methyl acrylate, ethyl acrylate, butyl acrylate, methyl methacrylate and the like; vinylidene monomers having one or more terminal $CH_2=CH-$ groups; vinyl aromatics such as divinylbenzene, diisopropenylbenzene, styrene, α-methylstyrene, bromostyrene, chlorostyrene, fluorostyrene and other such alkenyl-substituted aromatics; α-olefins such as ethylene, propylene, 1-butene and the like; vinyl halides, such as vinylbromide, chloroethane (vinylchloride), vinylfluoride, vinyliodide, 1,2-dibromoethene, 1,1-dichloroethene (vinylidene chloride), 1,2-dichloroethene and the like; vinyl esters, such as vinyl acetate; α,β-olefinically unsaturated nitriles, such as acrylonitrile and methacrylonitrile; α,β-olefinically unsaturated amides, such as acrylamide, N-methyl acrylamide, N,N-dimethylacrylamide, methacrylamide and the like.

Functionalized rubbery polymers which are copolymers of a functionalized monomer with one or more conjugated diene monomers, or with one or more other ethylenically unsaturated monomers, such as vinyl aromatic monomers, will normally contain from about 0.1 weight percent to about 10 weight percent functionalized monomer. The remaining weight percent of the comonomer or the combined comonomers may range from about 99.9 weight percent to about 90 weight percent.

Vinyl aromatic monomers are probably the most important group of ethylenically unsaturated monomers, which are commonly incorporated into polydiene rubbers. Such vinyl aromatic monomers are, of course, selected so as to be copolymerizable with the functionalized monomers being utilized. Generally, any vinyl aromatic monomer that is known to polymerize with organolithium initiators can be used. Such vinyl aromatic monomers typically contain from 8 to 20 carbon atoms. Usually, the vinyl aromatic monomer will contain from 8 to 14 carbon atoms. The most widely used vinyl aromatic monomer is styrene. Some examples of vinyl aromatic monomers that can be utilized include divinylbenzene, diisopropenylbenzene, styrene, 1-vinylnaphthalene, 2-vinylnaphthalene, α-methylstyrene, 4-phenylstyrene, 3-methylstyrene and the like.

Some representative examples of rubbery polymers that can be functionalized with the functionalized monomers of this invention include polybutadiene, polyisoprene, styrene-butadiene rubber (SBR), α-methylstyrene-butadiene rubber, α-methylstyrene-isoprene rubber, styrene-isoprene-butadiene rubber (SIBR), styrene-isoprene rubber (SIR), isoprene-butadiene rubber (IBR), α-methyl styrene-isoprene-butadiene rubber and α-methylstyrene-styrene-isoprene-butadiene rubber. In cases where the rubbery polymer is comprised of repeat units that are derived from two or more monomers, the repeat units which are derived from the different monomers, including the functionalized monomers, will normally be distributed in an essentially random manner. The repeat units that are derived from the monomers differ from the monomer in that a double bond is normally consumed in by the polymerization reaction.

The functionalized rubbery polymer can be made by solution polymerization in a batch process or in a continuous process by continuously charging at least one conjugated diene monomer or vinyl aromatic monomer, the functionalized monomer, and any additional monomers into a polymerization zone. The polymerization zone will typically be a polymerization reactor or a series of polymerization reactors. The polymerization zone will normally provide agitation to keep the monomers, polymer, initiator, and modifier well dispersed throughout the organic solvent the polymerization zone. Such continuous polymerizations are typically conducted in a multiple reactor system. The functionalized rubbery polymer synthesized is continuously withdrawn from the polymerization zone. The monomer conversion attained in the polymerization zone will normally be at least about 85 percent. In one example, the monomer conversion may be at least about 90 percent. The polymerization can be initiated with an anionic initiator, such as an alkyl lithium compound, or a Zeigler-Natta catalyst. The alkyl lithium compounds that can be used can contain from 1 to about 8 carbon atoms, such as n-butyl lithium.

The polymerization will also be conducted in the presence of an alkali metal alkoxide. The alkali metal alkoxide employed will typically be of the structural formula: M-O—R wherein M represents an alkali metal and wherein R represents an alkyl group (including cycloalkyl groups), an aryl group, an alkaryl group, or an arylalkyl group. The alkali metal will normally be a metal from Group I of the Periodic Table with lithium, sodium and potassium being preferred. Some representative examples of alkali metal alkoxides that can be used include: lithium methoxide, lithium ethoxide, lithium isopropoxide, lithium n-butoxide, lithium sec-butoxide, lithium t-butoxide, lithium 1,1-dimethylpropoxide, lithium 1,2-dimethylpropoxide, lithium 1,1-dimethylbutoxide, lithium 1,10-dimethylpentoxide, lithium 2-ethylhexanoxide, lithium 1-methylheptoxide, lithium phenoxide, lithium p-methylphenoxide, lithium p-octylphenoxide, lithium p-nonylphenoxide, lithium p-dodecylphenoxide, lithium α-naphthoxide, lithium β-naphthoxide, lithium o-methoxyphenoxide, lithium o-methoxyphenoxide, lithium m-methoxyphenoxide, lithium p-methoxyphenoxide, lithium o-ethoxyphenoxide, lithium 4-methoxy-1-naphthoxide, sodium methoxide, sodium ethoxide, sodium isopropoxide, sodium n-butoxide, sodium sec-butoxide, sodium t-butoxide, sodium 1,1-dimethylpropoxide, sodium 1,2-dimethylpropoxide, sodium 1,1-dimethylbutoxide, sodium 1,10-dimethylpentoxide, sodium 2-ethylhexanoxide, sodium 1-methylheptoxide, sodium phenoxide, sodium p-methylphenoxide, sodium p-octylphenoxide, sodium p-nonylphenoxide, sodium p-dodecylphenoxide, sodium α-naphthoxide, sodium β-naphthoxide, sodium o-methoxyphenoxide, sodium o-methoxyphenoxide, sodium m-methoxyphenoxide, sodium p-methoxyphenoxide, sodium o-ethoxyphenoxide, sodium 4-methoxy-1-naphthoxide, potassium methoxide, potassium ethoxide, potassium isopropoxide, potassium n-butoxide, potassium sec-butoxide, potassium t-butoxide, potassium 1,1-dimethylpropoxide, potassium 1,2-dimethylpropoxide, potassium 1,1-dimethylbutoxide, potassium 1,10-dimethylpentoxide, potassium 2-ethylhexanoxide, potassium 1-methylheptoxide, potassium phenoxide, potassium p-methylphenoxide, potassium p-octylphenoxide, potassium p-nonylphenoxide, potassium p-dodecylphenoxide, potassium α-naphthoxide, potassium β-naphthoxide, potassium o-methoxyphenoxide, potassium o-methoxyphenoxide, potassium m-methoxyphenoxide, potassium p-methoxyphenoxide, potassium o-ethoxyphenoxide, potassium 4-methoxy-1-naphthoxide, and the like.

The alkali metal alkoxide may be an alkali metal salt of a cyclic alcohol. In one example, the metal salt of the cyclic alcohol is a Group Ia metal salt. Lithium, sodium, potassium, rubidium, and cesium salts are representative examples of such salts with lithium, sodium, and potassium salts being preferred. Sodium salts are typically the most preferred. The cyclic alcohol can be mono-cyclic, bi-cyclic or tri-cyclic and can be aliphatic or aromatic. The cyclic alcohol can be substituted with 1 to 5 hydrocarbon moieties and can also optionally contain hetero-atoms. For instance, the metal salt of the cyclic alcohol can be a metal salt of a di-alkylated cyclohexanol, such as 2-isopropyl-5-methylcyclohexanol or 2-t-butyl-5-methylcyclohexanol. These salts are generally preferred because they are soluble in hexane. Metal salts of disubstituted cyclohexanol are highly preferred because they are soluble in hexane and provide similar modification efficiencies to sodium t-amylate. Sodium mentholate is the most highly preferred metal salt of a cyclic alcohol that can be employed. Metal salts of thymol can also be utilized. The metal salt of the cyclic alcohol can be prepared by reacting the cyclic alcohol directly with the metal or another metal source, such as sodium hydride, in an aliphatic or aromatic solvent. Some representative examples of alcohols which can be utilized in preparing the lithium alkoxide include t-butanol, sec-butanol, cyclohexanol, octanol, 2-ethylhexanol, p-cresol, m-cresol, nonylphenol, hexylphenol, tetrahydrofuryl alcohol, furfuryl alcohol, and tetrahydrofurfuryl, and the like.

The molar ratio of the alkali metal alkoxide to the lithium initiator will typically be within the range of about 0.001:1 to about 2:1. In another example, the molar ratio of the alkali metal alkoxide to the lithium initiator is within the range of about 0.005:1 to about 1:1. In another example, the molar ratio of the alkali metal alkoxide to the lithium initiator is within the range of about 0.008:1 to about 0.3:1.

The polymerization temperature utilized can vary over a broad range of from about −20° C. to about 180° C. In one example, a polymerization temperature within the range of about 30° C. to about 125° C. will be utilized. In another example, the polymerization temperature is within the range of about 45° C. to about 100° C. In another example, the polymerization temperature is within the range of about 60° C. to about 90° C. The pressure used will normally be sufficient to maintain a substantially liquid phase under the conditions of the polymerization reaction.

The polymerization is conducted for a length of time sufficient to permit substantially complete polymerization of monomers. In other words, the polymerization is generally carried out until high conversions of at least about 85 percent are attained. The polymerization is then terminated by the addition of an agent, such as an alcohol, a terminating agent, or a coupling agent. For example, a tin halide and/or silicon halide can be used as a coupling agent. The tin halide and/or the silicon halide are continuous added in cases where asymmetrical coupling is desired. This continuous addition of tin coupling agent and/or the silicon coupling agent is normally done in a reaction zone separate from the zone where the bulk of the polymerization is occurring. The coupling agents will typically be added in a separate reaction vessel after the desired degree of conversion has been attained. The coupling agents can be added in a hydrocarbon solution, e.g., in cyclohexane, to the polymerization admixture with suitable mixing for distribution and reaction. In other words, the coupling will typically be added only after a high degree of conversion has already been attained. For instance, the coupling agent will normally be added only after a monomer conversion of greater than about 85 percent has been realized. In one example, the monomer conversion reaches at least about 90 percent before the coupling agent is added.

The tin halides used as coupling agents can be tin tetrahalides, such as tin tetrachloride, tin tetrabromide, tin tetrafluoride or tin tetraiodide. However, tin trihalides can also optionally be used. Polymers coupled with tin trihalides having a maximum of three arms. This is, of course, in contrast to polymers coupled with tin tetrahalides which have a maximum of four arms. To induce a higher level of branching, tin tetrahalides are normally preferred. As a general rule, tin tetrachloride is most preferred.

The silicon coupling agents that can be used include silicon tetrahalides, such as silicon tetrachloride, silicon tetrabromide, silicon tetrafluoride or silicon tetraiodide. However, silicon trihalides can also optionally be used. Polymers coupled with silicon trihalides having a maximum of three arms. This is, of course, in contrast to polymers coupled with silicon tetrahalides which have a maximum of four arms. To induce a higher level of branching, silicon tetrahalides may be used.

A combination of a tin halide and a silicon halide can optionally be used to couple the rubbery polymer. By using such a combination of tin and silicon coupling agents improved properties for tire rubbers, such as lower hysteresis, can be attained. In one example, a combination of tin and silicon coupling agents can be used in tire tread compounds that contain both silica and carbon black. In such cases, the molar ratio of the tin halide to the silicon halide employed in coupling the rubbery polymer may be within the range of 20:80 to 95:5. In one example, the molar ratio of the tin halide to the silicon halide employed in coupling the rubbery polymer is within the range of 40:60 to 90:10. In another example, the molar ratio of the tin halide to the silicon halide employed in coupling the rubbery polymer is within the range of 60:40 to 85:15. In yet another example, the molar ratio of the tin halide to the silicon halide employed in coupling the rubbery polymer is within the range of 65:35 to 80:20.

A range of about 0.01 to 4.5 milliequivalents of tin coupling agent (tin halide and silicon halide) may be employed per 100 grams of the rubbery polymer. In one example, about 0.01 to about 1.5 milliequivalents of the coupling agent per 100 grams of polymer may be used to obtain the desired Mooney viscosity. Larger quantities tend to result in production of polymers containing terminally reactive groups or insufficient coupling. One equivalent of tin coupling agent per equivalent of lithium is generally considered an optimum amount for maximum branching. For instance, if a mixture tin tetrahalide and silicon tetrahalide is used as the coupling agent, one mole of the coupling agent would be utilized per four moles of live lithium ends. In cases where a mixture of tin trihalide and silicon trihalide is used as the coupling agent, one mole of the coupling agent will optimally be utilized for every three moles of live lithium ends. The coupling agent can be added in a hydrocarbon solution, e.g., in cyclohexane, to the polymerization admixture in the reactor with suitable mixing for distribution and reaction.

After the coupling has been completed, a tertiary chelating alkyl 1,2-ethylene diamine or a metal salt of a cyclic alcohol can optionally be added to the polymer cement to stabilize the coupled rubbery polymer.

In most cases, from about 0.01 phr (parts by weight per 100 parts by weight of dry rubber) to about 2 phr of the chelating alkyl 1,2-ethylene diamine or metal salt of the cyclic alcohol will be added to the polymer cement to stabilize the rubbery polymer. Typically, from about 0.05 phr to about 1 phr of the chelating alkyl 1,2-ethylene diamine or metal salt of the cyclic alcohol will be added. More typically, from about 0.1 phr to about 0.6 phr of the chelating alkyl 1,2-ethylene diamine or the metal salt of the cyclic alcohol will be added to the polymer cement to stabilize the rubbery polymer.

The terminating agents that can be used to stop the polymerization and to "terminate" the living rubbery polymer include tin monohalides, silicon monohalides, N,N,N',N'-tetradialkydiamino-benzophenones (such as tetramethyldiaminobenzophenone and the like), N,N-dialkylamino-benzaldehydes (such as dimethylaminobenzaldehyde and the like), 1,3-dialkyl-2-imidazolidinones (such as 1,3-dimethyl-2-imidazolidinone and the like), 1-alkyl substituted pyrrolidinones; 1-aryl substituted pyrrolidinones, dialkyl-dicycloalkyl-carbodiimides containing from about 5 to about 20 carbon atoms, and dicycloalkyl-carbodiimides containing from about 5 to about 20 carbon atoms.

After the termination step, and optionally the stabilization step, has been completed, the rubbery polymer can be recovered from the organic solvent. The coupled rubbery polymer can be recovered from the organic solvent and residue by means such as chemical (alcohol) coagulation, thermal desolventization, or other suitable method. For instance, it is often desirable to precipitate the rubbery polymer from the organic solvent by the addition of lower alcohols containing from about 1 to about 4 carbon atoms to the polymer solution. Suitable lower alcohols for precipitation of the rubber from the polymer cement include methanol, ethanol, isopropyl alcohol, normal-propyl alcohol and t-butyl alcohol. The utilization of lower alcohols to precipitate the rubbery polymer from the polymer cement also "terminates" any remaining living polymer by inactivating lithium end groups. After the coupled rubbery polymer is recovered from the solution, steam-stripping can be employed to reduce the level of volatile organic compounds in the coupled rubbery polymer.

Additionally, the organic solvent can be removed from the rubbery polymer by drum drying, extruder drying, vacuum drying, and the like.

The functionalized rubbery polymers of the present invention can be used alone or in combination with other elastomers to prepare a rubber compound, such as a tire treadstock, sidewall stock or other tire component stock compounds. In a tire, at least one such component is produced from a vulcanizable elastomeric or rubber composition. For example, the functionalized rubbery polymer made can be blended with any conventionally employed treadstock rubber which includes natural rubber, synthetic rubber and blends thereof. Such rubbers are well known to those skilled in the art and include synthetic polyisoprene rubber, styrene/butadiene rubber (SBR), polybutadiene, butyl rubber, Neoprene, ethylene/propylene rubber, ethylene/propylene/diene rubber (EPDM), acrylonitrile/butadiene rubber (NBR), silicone rubber, the fluoroelastomers, ethylene acrylic rubber, ethylene vinyl acetate copolymer (EVA), epichlorohydrin rubbers, chlorinated polyethylene rubbers, chlorosulfonated polyethylene rubbers, hydrogenated nitrile rubber, tetrafluoroethylene/propylene rubber and the like.

When the rubbery polymers are blended with conventional rubbers, the amounts can vary widely such as between 10 and 99 percent by weight. In any case, tires made with synthetic rubbers that are synthesized utilizing the techniques of this invention exhibit decreased rolling resistance. Desirable benefits can be realized in cases where the tire tread compound is made with the rubbery polymer synthesized utilizing the technique of this invention. However, desirable benefits can also by attained in cases where at least one structural element of the tire, such as subtread, sidewalls, body ply skim, or bead filler, is comprised of the functionalized rubbery polymer.

The synthetic rubbers made in accordance with embodiments of this invention can be compounded with carbon black in amounts ranging from about 5 to about 100 phr (parts by weight per 100 parts by weight of rubber). In one example, about 5 to about 80 phr may be used. In another example, about 40 to about 70 phr may be used. The carbon blacks may include any of the commonly available, commercially-produced carbon blacks but those having a surface area (EMSA) of at least 20 m$^2$/g. In one example, at least 35 m$^2$/g up to 200 m$^2$/g or higher surface area is used. Surface area values used in this application are those determined by ASTM test D-1765 using the cetyltrimethyl-ammonium bromide (CTAB) technique. Among the useful carbon blacks are furnace black, channel blacks and lamp blacks. More specifically, examples of the carbon blacks include super abrasion furnace (SAF) blacks, high abrasion furnace (HAF) blacks, fast extrusion furnace (FEF) blacks, fine furnace (FF) blacks, intermediate super abrasion furnace (ISAF) blacks, semi-reinforcing furnace (SRF) blacks, medium processing channel blacks, hard processing channel blacks and conducting channel blacks. Other carbon blacks which may be utilized include acetylene blacks. Mixtures of two or more of the above blacks can be used in preparing the carbon black products of the invention.

The carbon blacks utilized in the preparation of rubber compounds may be in pelletized form or an unpelletized flocculent mass. For more uniform mixing, unpelletized carbon black may be used. The reinforced rubber compounds can be cured in a conventional manner with about 0.5 to about 4 phr of known vulcanizing agents. For example, sulfur or peroxide-based curing systems may be employed. For a general disclosure of suitable vulcanizing agents one can refer to Kirk-Othmer, Encyclopedia of Chemical Technology, 3rd ed., Wiley Interscience, N.Y. 1982, Vol. 20, pp. 365-468, particularly "Vulcanization Agents and Auxiliary Materials" pp. 390-402. Vulcanizing agents can, of curse, be used alone or in combination. Vulcanizable elastomeric or rubber compositions can be prepared by compounding or mixing the polymers thereof with carbon black and other conventional rubber additives such as fillers, plasticizers, antioxidants, curing agents and the like, using standard rubber mixing equipment and procedures and conventional amounts of such additives.

Non-limiting examples of functionalized monomers with sulfur, phosphorus, and silicon in accordance with the description are now disclosed below. These examples are merely for the purpose of illustration and are not to be regarded as limiting the scope of the invention or the manner in which it can be practiced. Other examples will be appreciated by a person having ordinary skill in the art.

Example I

A three-liter round bottom flask containing one mole of divinylbenzene and 30 mmoles of n-butyl lithium, which was cooled to 5° C., was charged with two liters of hexane and one mole of N,N-dimethylaminoethyl thiol. After one hour, the mixture was neutralized with 30 mmoles of isopropyl alcohol then placed in a rotary evaporator to remove all the solvent. The remaining residue was vacuum distilled with hydroxyl 3,3,5,5 tetramethyl-1-pyrolline-N-oxide (TMPO) as a gel preventive. The final product was N,N-dimethylaminoethylthio ethylstyrene, which was identified by C13 NMR.

Example II

The same procedure above was repeated using divinylbenzene with n-butyl lithium as the catalyst, and hexane. Rather than N,N-dimethylaminoethyl thiol, one mole of N,N-dimethylaminoethyl phosphorus hydride was added to the mixture. The resulting product after vacuum distillation was identified as N,N-dimethylaminoethyl phosphorus ethylstyrene.

Example III

The same procedure above was repeated using divinylbenzene with n-butyl lithium as the catalyst, and hexane. Rather than N,N-dimethylaminoethyl thiol, 3-aminopropyltriphenoxysilane was added to the mixture. The resulting product after vacuum distillation was identified as aminopropyltriphenoxysilane ethylstyrene, which was identified by C13 NMR.

The same procedure above may be followed to make various types of functional monomers in accordance with the invention. The prepared functionalized monomer, for example, may be copolymerized with styrene-butadiene.

The polymers so formed from the functionalized monomers of the present invention thus can be used to provide functionalized rubbery polymers which, in turn, can provide tire treads with good wet skid resistance, low rolling resistance, tear strength and good wear characteristics, without sacrificing wet skid resistance and traction characteristics.

While the present invention has been illustrated by the description of embodiments, and while the illustrative embodiments have been described in considerable detail, it is not the intention of the inventors to restrict or in anyway limit the scope of the appended claims to such detail. Additional advantages and modifications readily will appear to those skilled in the art. The invention in its broader aspects is therefore not limited to the specific details, representative apparatus and methods, and illustrative examples shown and described. Accordingly, departures may be made from such details without departing from the scope of the inventors' general inventive concept.

What is claimed is:

1. A functionalized monomer having a structure according to the following formula:

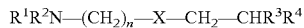

wherein $R^1$ and $R^2$ are independently selected from a group consisting of alkyls, cycloalkyls, alkenyls, cycloalkenyls, aryls, phenyls, heterocycles, acyls, and silyls; or $R^1$ in combination with $R^2$ forms a heterocyclic ring;
n is an integer from 1 to 20;
X is a phosphorus moiety or a silicon moiety;
$R^3$ and $R^4$ are selected from the groups consisting of hydrogen, alkyls, alkenyls, and aryls; and
at least one of $R^3$ and $R^4$ contain reactive unsaturation.

2. The functionalized monomer of claim 1 wherein $R^1$ and $R^2$ are the same or different and are selected from the group consisting of $C_1$-$C_{10}$ alkyl, oxygen substituted $C_1$-$C_{10}$ alkyl, and nitrogen substituted $C_1$-$C_{10}$ alkyl.

3. The functionalized monomer of claim 1 wherein $R^1$ and $R^2$ represent a heterocyclic ring selected from the group of aziridine, azetidine, diazetidine, pyrrolidine, piperidine, piperazine, or morpholine moiety.

4. The functionalized monomer of claim 1 wherein $R^3$, $R^4$, or both are an aryl group at least one of which is substituted with an alkenyl moiety.

5. The functionalized monomer of claim 1 wherein $R^3$ is either hydrogen or methyl; and $R^4$ is a aryl moiety substituted in the ortho, meta, or para position with an alkenyl moiety selected from the group consisting of ethylene and isopropylene.

6. The functionalized monomer of claim 5 wherein $R^1$ and $R^2$ are selected from the group consisting of methyl, ethyl, propyl, butyl, pentyl, hexyl, phenyl, or benzyl.

7. A functionalized monomer having a structure according to the following formula:

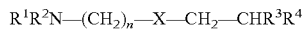

wherein $R^1$ and $R^2$ represent a heterocyclic ring selected from the group of aziridine, azetidine, diazetidine, pyrrolidine, piperidine, piperazine, or morpholine moiety;
n is an integer from 1 to 20;
X is selected from a group consisting of sulfur, a phosphorus moiety, and a silicon moiety;
$R^3$ and $R^4$ are selected from the groups consisting of hydrogen, alkyls, alkenyls, and aryls; and
at least one of $R^3$ and $R^4$ contain reactive unsaturation.

8. A functionalized monomer having a structure according to the following formula:

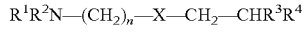

wherein $R^1$ and $R^2$ are independently selected from a group consisting of alkyls, cycloalkyls, alkenyls, cycloalkenyls, aryls, phenyls, heterocycles, acyls, and silyls; or $R^1$ in combination with $R^2$ forms a heterocyclic ring;
n is an integer from 1 to 20;
X is selected from a group consisting of sulfur, a phosphorus moiety, and a silicon moiety; and
$R^3$ and $R^4$ are selected from the group consisting of hydrogen, alkyls, alkenyls, and aryls, wherein at least one of $R^3$ and $R^4$ contain reactive unsaturation and wherein $R^3$, $R^4$, or both are an aryl group, at least one of which is substituted with an alkenyl moiety.

9. A functionalized monomer having a structure according to the following formula:

$R^1R^2N$—$(CH_2)_n$—$X$—$CH_2$—$CHR^3R^4$ wherein $R^1$ and $R^2$ are independently selected from a group consisting of alkyls, cycloalkyls, alkenyls, cycloalkenyls, aryls, phenyls, heterocycles, acyls, and silyls; or $R^1$ it in combination with $R^2$ forms a heterocyclic ring;
n is an integer from 1 to 20;
X is selected from a group consisting of sulfur, a phosphorus moiety, and a silicon moiety;
$R^3$ is either hydrogen or methyl; and
$R^4$ is an aryl moiety substituted in the ortho, meta, or para position with an alkenyl moiety selected from the group consisting of ethylene and isopropylene.

10. The functionalized monomer of claim 9 wherein $R^1$ and $R^2$ are selected from the group consisting of methyl, ethyl, propyl, butyl, pentyl, hexyl, phenyl, or benzyl.

11. A functionalized rubbery polymer wherein said functionalized rubbery polymer is a polymer of at least one conjugated diene monomer or vinyl aromatic monomer, and a functionalized monomer having a structure according to the following formula:

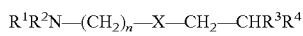

wherein $R^1$ and $R^2$ are independently selected from a group consisting of alkyls, cycloalkyls, alkenyls, cycloalkenyls, aryls, phenyls, heterocycles, acyls, and silyls; or $R^1$ in combination with $R^2$ forms a heterocyclic ring;
n is an integer from 1 to 20;
X is selected from a group consisting of sulfur, a phosphorus moiety, and silicon moiety;
$R^3$ and $R^4$ are selected from the group consisting of hydrogen, alkyls, alkenyls, and aryls; and at least one of $R^3$ and $R^4$ contain reactive unsaturation; and
said functionalized monomer is present in about 0.1 percent by weight to about 10 percent by weight of said functionalized rubbery polymer.

12. The functionalized rubbery polymer of claim 11 wherein the conjugated diene monomer is selected from a group consisting of isoprene and butadiene; and the vinyl aromatic monomer is selected from a group consisting of styrene, divinylbenzene, and diisopropenylbenzene.

13. The functionalized rubbery polymer of claim 11 wherein $R^1$ and $R^2$ may be the same or different and represent an alkyl group containing from about 1 to 10 carbons which is optionally substituted with oxygen or nitrogen.

14. The functionalized rubbery polymer of claim 11 wherein $R^1$ and $R^2$ represent a heterocyclic ring selected from the group consisting of aziridine, azetidine, diazetidine, pyrrolidine, piperidine, piperazine, or morpholine moiety.

15. The functionalized rubbery polymer of claim 11 wherein at least one of $R^3$ and $R^4$, is an aryl group which is optionally substituted in the ortho, meta, or para position with an alkenyl moiety.

16. The functionalized rubbery polymer of claim 11 wherein $R^3$ is either hydrogen or methyl; and $R^4$ is a aryl moiety substituted with an alkenyl moiety selected from the group consisting of ethylene and isopropylene.

17. The functionalized rubbery polymer of claim 11 wherein $R^1$ and $R^2$ are selected from the group consisting of methyl, ethyl, propyl, butyl, pentyl, hexyl, phenyl, or benzyl.

18. A method comprising:
polymerizing at least one conjugated diene monomer or vinyl aromatic monomer with a functionalized monomer having a structure according to the following formula:

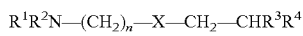

wherein $R^1$ and $R^2$ are independently selected from a group consisting of alkyls, cycloalkyls, alkenyls, cycloalkenyls, aryls, phenyls, heterocycles, acyls, and silyls; or $R^1$ in combination with $R^2$ forms a heterocyclic ring;

n is an integer from 1 to 20;

X is selected from a group consisting of sulfur, a phosphorus moiety, and a silicon moiety;

$R^3$ and $R^4$ are selected from a group consisting of hydrogen, alkyls, alkenyls, and aryls; and at least one of $R^3$ and $R^4$ contain reactive unsaturation.

19. The method of claim 18 wherein the conjugated diene monomer is selected from a group consisting of isoprene and butadiene; and the vinyl aromatic monomer is selected from a group consisting of styrene, divinylbenzene, and diisopropenylbenzene.

20. The method of claim 18 further comprising a solvent and an initiator system.

21. The method of claim 20 wherein the solvent is water, and the initiator system comprises a peroxide.

22. The method of claim 20 wherein the solvent is an organic solvent, and the initiator system comprises an organometallic reagent.

* * * * *